United States Patent [19]

Holly

[11] Patent Number: 4,883,658
[45] Date of Patent: Nov. 28, 1989

[54] OPHTHALMIC SOLUTION FOR TREATMENT OF DRY-EYE SYNDROME

[76] Inventor: Frank J. Holly, 301 York Ave., Lubbock, Tex. 79416

[21] Appl. No.: 194,215

[22] Filed: May 16, 1988

Related U.S. Application Data

[63] Continuation of Ser. No. 856,531, Apr. 28, 1986, Pat. No. 4,744,980.

[51] Int. Cl.$^4$ .................. A61K 31/74; A61K 31/79
[52] U.S. Cl. .................................. 424/80; 424/78; 514/915
[58] Field of Search .................. 424/78, 80; 514/915

[56] References Cited

U.S. PATENT DOCUMENTS

| | | | |
|---|---|---|---|
| 3,767,789 | 10/1973 | Rankin | 424/78 |
| 3,856,919 | 12/1974 | Rankin | 424/78 |
| 3,868,445 | 2/1975 | Ryde et al. | 424/429 |
| 3,907,985 | 9/1975 | Rankin | 424/78 |
| 3,920,810 | 12/1975 | Rankin | 424/80 |
| 3,947,573 | 3/1976 | Rankin | 424/80 |
| 3,968,201 | 7/1976 | Ryde et al. | 424/78 |
| 3,987,163 | 10/1976 | Rankin | 424/78 |
| 3,991,759 | 11/1976 | Urquhart | 128/260 |
| 4,039,662 | 8/1977 | Hecht et al. | 424/180 |
| 4,120,949 | 10/1978 | Bapatta et al. | 424/78 |
| 4,131,651 | 12/1978 | Shah et al. | 424/78 |
| 4,271,144 | 6/1981 | Holly | 424/78 |
| 4,343,787 | 8/1982 | Katz | 424/78 |
| 4,409,205 | 10/1983 | Shively | 424/78 |
| 4,529,535 | 7/1985 | Sherman | 252/106 |
| 4,560,491 | 12/1985 | Sherman | 252/106 |
| 4,744,980 | 5/1988 | Holly | 424/78 |

OTHER PUBLICATIONS

Lemp–"Tear Substitute in the Treatment of Dry Eyes'-'—Int. Ophthal. Clin. 13, 145–153 (1973).
International Search Report PCT/US80?00696.
Holly, "Clinical Pharmacology of the Anterior Segment", Int. Ophtal. Clin., No. 3, vol. 20, 171–185 (1980).
Holly, "Surface Chemical Evaluation of Artificial Tears and Their Ingredients. III Dynamic Properties", Contact and Intraocular Lens Medical Journal, vol. 5, No. 1, pp. 21–33, Jan., Mar. 1979.
Holly "Surface Chemical Evaluation of Artificial Tears and Their Ingredients. II Interaction with a Superficial Lipid Layer", Contact and Intraocular Lens Medical Journal, vol. 4, No. 3, pp. 52–65, Jul.–Sep. 1978.
Holly, "Surface Chemical Evaluation of Artificial Tears and their Ingredients. I Interfacial Activity at Equilibrium", Contact & Intraocular Lens Medical Journal, vol. 4, No. 2, pp. 14–31, Apr.–Jun. 1978.
Holly–"Physical Chemistry of the Normal and Disordered Tear Film", Trans. Optham. Soc. U.K., 104, pp. 374–380 (1985).
Holly, "Biophysical Aspects of Epithelial Adhesions to Stroma", Investigative Ophtalmology & Visual Science, vol. 17, No. 6, pp. 552–557, 1978.

*Primary Examiner*—Douglas W. Robinson
*Assistant Examiner*—Joseph A. Lipovsky
*Attorney, Agent, or Firm*—Charmasson & Holz

[57] ABSTRACT

A synergistic combination of an aqueous solution of a partially hydrolyzed poly(vinyl acetate) and a fully hydrolyzed poly(vinyl acetate), i.e. poly(vinyl alcohol), exhibiting a low surface tension at the water-air interface, while forming a completely wettable absorbed layer over hydrophobic solids. The combination is used as part of an ophthalmic solution including a hydrophilic low viscosity polymer, poly(N-glucose) or poly(N-vinyl pyrrolidone) with higher than normal oncotic pressure in a physiologically compatible electrolytic solution base. The formulation is effective in treating the two major underlying causes of the dry eye syndrome; ocular surface disorder and tear film abnormalities resulting in tear film instability. It can also be effective as an aqueous vehicle for topically used ophthalmic drugs or nutrients.

4 Claims, No Drawings

OPHTHALMIC SOLUTION FOR TREATMENT OF DRY-EYE SYNDROME

PRIOR APPLICATION

This is a continuation of co-pending patent application Ser. No. 856,531 filed Feb. 28, 1986 now U.S. Pat. No. 4,744,980.

FIELD OF THE INVENTION

This invention relates to film-forming compounds and particularly to ophthalmic solutions. More specifically this invention relates to the treatment of ocular surface disorders and tear film abnormalities. That part of the invention which teaches how to obtain a solution with sufficiently low surface tension while forming a highly water wettable adsorbed layer over a hydrophobic solid can be applied to the preparation of wetting solutions for contact lenses and to improve the efficiency of other surface-active compounds such as pesticides, herbicides, and certain protective coatings.

BACKGROUND OF THE INVENTION

The classical and devastating dry eye states historically are xerophthalmia and keratomalacia. These grave conditions are caused by dietary deficiencies especially lack of protein and avitaminosis A and invariably lead to blindness. Fortunately, these grave diseases are rare in the technologically developed countries including the United States but still are fairly common in the third world countries.

Unfortunately, the population of the developed countries is not free of the "drying of the eye". It has been recognized only in the last decade that many of the eye complaints related to persistent irritation, burning sensation, conjunctival vasodilation, inflammatory reaction, occasional excessive tearing, and photophobia are usually caused by a dry eye state. Recent progress in tear film physiology enabled us to elucidate the underlying causes of such nonspecific and often marginal dry eye conditions which can be traced to certain tear film abnormalities resulting in pathological instability of the tear film over the corneal surface. Such tear film instability can and usually does cause pathological changes in the underlying epithelium. The resulting epitheliopathy further diminishes tear film stability, which in turn degrades the epithelial surface even more. Primary ocular surface disorder can also cause tear film instability which then enhances the gravity of the surface disorder.

The mainstay of the treatment of the dry eye conditions since antiquity has been the topical instillation of lubricating and wetting eye drops, tear substitutes or artificial tears. It is, however, important to realize that the tear secretion rate is pathologically diminished only in a relatively small fraction of the patients suffering from some dry eye state. Often stable tear film cannot be formed over the ocular surface despite an adequate amount of tears. Hence, the artificial tear formulations should not only supplement deficient fluid but should be capable of increasing tear film stability by forming stable fluid films over the ocular surface. These formulations should also have a beneficial effect on existing surface epitheliopathy, since such a pathology adversely affects fluid film stability.

DESCRIPTION OF THE PRIOR ART

Artificial tears that have been developed previously for replacement of deficient tears and for the treatment of the dry eye syndrome consist of isotonic or hypotonic aqueous solutions of crystalloids, usually electrolytes or low molecular weight carbohydrates, and some modified natural gums or synthetic polymers. The formulations also contain a preservative system with bacteriostatic or bacteriocidal properties. The role of the polymer(s) traditionally has been to increase viscosity and thereby retention time. Consequently it has been shown that viscosity only improves retention time if its value is quite high. Since the tear film also serves as a lubricant for the moving eye lids during blinking, and since increased viscosity interferes with lubrication, there is a practical upper limit above which viscosity cannot be increased and thus retention time cannot be enhanced. More recently, polymeric components were also claimed to have a stabilizing effect on the tear film and these claims were occasionally substantiated by in vitro experimental data. Until now the overall effect of the tear substitute components on this aqueous film stability as well as the effect on the superficial lipid layer of the tear film have not been considered by the formulators. As a result, none of the commercially available tear substitutes are capable of forming a stable fluid film over hydrophobic surfaces such as the corneal epithelium and some have a detrimental effect on the superficial lipid layer of the tear film.

U.S. Pat. Nos. 3,767,788, 3,856,919 and 3,947,573 all to Rankin describe an ophthalmic solution which includes high and optionally low molecular weight poly(ethylene oxide)s which due to the numerous etheric oxygen bonds in the molecule are quite hydrophilic and also impart viscosity and pituitousness to the solution. The last patent also claims that the formulation has properties favorable as an ophthalmic drug-carrying vehicle.

U.S. Pat. No. 3,767,789 Rankin claims that poly(ethylene oxide) having a molecular weight of at least 100,000 daltons in aqueous solution behaves and performs as a synthetic mucus thereby it is capable of supplementing conjunctival mucus which is recognized as the natural wetting and film-stabilizing agent for the preocular tear film.

U.S. Pat. Nos. 3,907,985 and 3,987,163 both to Rankin describe an ophthalmic formulation the main ingredient of which is poly(styrene sulfonate) of medium to high molecular weight and which only optionally contains poly(ethylene glycol) or poly(propylene glycol) of low molecular weight. Although mucus-like behavior is mentioned briefly, such a behavior is not substantiated. On the contrary, the main role of poly(styrene sulfonate) appears to be viscosity-building.

U.S. Pat. No. 3,920,810 Rankin describes another ophthalmic formulation where the main ingredient is poly(acrylamide) and which optionally contains poly(ethylene glycol). The solution is claimed to have lubricating and cushioning properties as well as serving as aqueous vehicles for ophthalmic drugs.

U.S. Pat. No. 4,039,662 Hecht and Shively describes an ophthalmic formulation containing a simple polysaccharide, preferably poly(N-glucose) which allegedly exhibits a synergistic effect in wetting when combined with a cationic surfactant and preservative, benzalkonium chloride and is capable of forming a relatively stable film over the corneal surface of excised rabbit eyes.

U.S. Pat. No. 4,271,144 Holly discloses an ophthalmic solution containing electrolytes at only isotonic levels and hydrophilic macromolecules at such concentration that their collodial osmotic pressure is equal or greater than the imbibition pressure of corneal stroma. The solution is primarily prescribed for dehydrating edematous cornea and as a protective corneal epithelium shield during tonographic or tonometric processes.

U.S. Pat. No. 4,409,205 Shively discusses an aqueous formulation which contains mostly nonionic tonicity adjusting agents and only low levels of electrolytes in addition to nonionic synthetic polymers such as polyvinyl alcohol and/or polyethylene glycol which is supposed to restructure the abnormal tear film and prevent the precipitation of protein-like substances from the aqueous tears.

U.S. Pat. No. 4,131,651 Shah and Sibley describe a novel composition consisting of a synergistic mixture of poly(vinyl alcohol) and a hydroxyalkylcellulose such as hydroxyethyl cellulose. They have determined various film-forming and retaining properties of the preparations containing different ratios of the two polymers over Plexi glass surfaces such as film thickness of solution attached to the plastic, dewetting time, surface viscosity, and surface tension. At the weight ratio of 4:1 of the cellulose ether and the polyvinyl alcohol the properties deemed relevant to tear film stability were optimized and this synergistic ratio was employed in formulating the tear substitute.

Several detailed studies have been published of the relevant surface chemical properties of the commercially available tear substitutes. It has been concluded that despite enhanced understanding of the basic factors controlling tear film stability and the role of macromolecular tear components in achieving film stability, the polymeric components of the tear substitutes are little more than viscosity-building agents. The favorable surface chemical properties are usually achieved by the incorporation of surface-active preservatives into the formulation, even though due to their low molecular weight these agents have a detrimental effect on the lipid layer and thus on the stability of the tear film. For example, none of the tear substitutes presently marketed are capable of forming a stable thin film over a hydrophobic solid surface similar in properties to the mucus-free epithelium. Furthermore, some of the formulations rapidly disperse overlying lipid films.

DESCRIPTION OF THE INVENTION

The present invention comprises an aqueous solution containing the synergistic mixture of two types of polyvinyl alcohol. Polyvinyl alcohol is manufactured by the controlled hydrolysis of polyvinyl acetate where the esteric group of the acetic acid is replaced by the alcoholic hydroxyl group. If at least 73% of the acetate groups is hydrolyzed the polymer is water-soluble. Thus, various types of polyvinyl alcohol exist depending on the degree of hydrolysis and thus the concentration of the remaining acetate groups on the hydrocarbon polymeric chain; Polyvinyl alcohol with high acetate content (but not more than 27%) is quite surface active and is capable of lowering the surface tension of water from 72 to 42 mN/m (for the sake of brevity this type of polyvinyl alcohols will sometimes be referred to as "polyvinyl acetates"). On the other hand, polyvinyl alcohol that is fully hydrolyzed (herein polyvinyl alcohol) exhibits almost no surface activity at the water-air interface. In general, the lower the surface tension of a liquid, the more it will wet a given solid surface. This tendency can be quantitated by the magnitude of the advancing contact angle of a solution droplet placed on the solid surface to be wetted.

However, the stability of a thin aqueous layer over a hydrophobic surface does not only depend on the surface tension of the solution. The other factor is the wettability of the solute layer that is adsorbed onto the solid surface and its effect on the water-solid interfacial tension. The receding contact angle of the solution on the solid surface is a measure of the wettability of the adsorbed layer of solute. Interestingly, the wettability of adsorbed polyvinyl alcohol layers varies inversely with the acetate content of the polymer, while the surface activity at the water-air interface increases with increasing acetate content. Thus, polyvinyl alcohol with negligible acetate content is completely wettable by the solution as evidenced by the zero receding contact angle, while acetate-containing polyvinyl alcohol (polyvinyl acetate) forms an adsorbed layer incompletely wettable by the solution despite its lower surface tension.

By mixing these two types of polyvinyl alcohol, one with negligible and one with considerable acetate content, it was found possible to lower the surface tension of the solution while forming a completely wettable adsorbed layer over hydrophobic solids. In fact at a certain weight ratio, these two properties will be optimized as evidenced in a minimum in the surface tension value which coincides with a zero receding contact angle value. Since effects related to surface activity are exhibited at low bulk concentration, it is possible to achieve the desired synergistic effect at fairly low polymer concentrations thereby avoiding increased viscosity which interferes with the lubricating role of the aqueous tears.

While the wettability of the adsorbed layer of polymer is important to promote fluid film stability, the adsorptivity of the polymer to the solid surface to be wetted is also important. When properly formulated according to the invention, the polymer adsorbs fairly tenaciously so that it cannot be easily rinsed off from a hydrophobic solid surface. However, when contaminated by hydrophobic lipids, it can be removed by the shear action of the lids.

Epitheliopathy secondary to tear film abnormalities usually is evidenced by adversely affected barrier properties of the epithelial layer. Damaged epithelium can become water-logged (microcystic edema) and lose its integrity and adhesiveness to the underlying stroma. Elevated oncotic pressure due to the presence of hydrophilic polymers at high concentration appears to have an ameliorating effect on damaged epithelium and on the degree of discomfort. Certain such polymers exhibit complexing properties toward nutrients or pharmacologically active agents. Thus, with proper formulation it is possible to increase the residence time of such agent over the ocular surface so that the same therapeutic response can be achieved by lower levels of the drug while the ocular surface is protected.

Hence, in addition to the synergistic mixture of polyvinyl alcohols the formulation invented also contains a hydrophilic polymer at sufficiently high concentration to achieve an oncotic pressure of at least 40 millimeters of mercury (mmHg) without unduly increasing the viscosity of the solution. Simple polysaccharides such as poly(N-glucose) or dextran are preferred when the molecular weight is such that the desired oncotic pressure can be achieved without excessively high solution concentration and concurrent increase in solution viscosity. When the formulation is to act as a nutrient or drug carrier, the third polymeric component should also have complexing properties in addition to having low viscosity. Then poly(N-vinyl pyrrolidone) (PVP) is preferred as such a third polymeric component.

The formulation should also contain inorganic electrolytes that are known to contribute to the well-being of the corneal epithelium. Specifically, the proper ratio of the alkali metal ions such as those of sodium, potassium or other monovalent metals at the physiological level as well as low levels of divalent alkaline earth metal ions such as those of calcium and magnesium appear to be necessary. The main corresponding anion is chloride as well as other carbonic acid anions defined by the buffer used. Among the buffers commonly used in ophthalmic formulations, those with sufficient inertness and stability can be chosen, as long as they are compatible with the polymeric components. Typically, a compatible buffer may consist of phosphates or phosphate and citrate anions with the corresponding alkali metals chosen to maintain the proper sodium-potassium ion ratio and at the proper dilution to prevent precipitation of alkali earth metal ions. The following examples further illustrate the various properties of the invention.

EXAMPLE I

It is known that certain hydrophilic polymers, that have a range of molecular weights and poorly defined chemical composition, can have widely differing surface chemical properties. Hence, samples of polyvinyl alcohols of various grades and acetate content were obtained from various manufacturers and tested for their effect on the surface tension of water, their effect on the wetting of a nonpolar solid such as glossy polyethylene (the advancing contact angle), and the wettability of their monomolecular layer adsorbed onto the nonpolar solid (the receding contact angle). Some of the results obtained are shown in Table I.

TABLE I

| Polyvinyl Alcohol [tradename-grade] | Acetate Content [percent] | Surface Tension [mN/m] | Contact Angle (degrees) | |
|---|---|---|---|---|
| | | | Advancing | Receding |
| Elvanol 90-50 | <1 | 62.6 | 78.8 | 0 |
| Elvanol 51-05 | 11.0–13.5 | 41.0 | 68.3 | 15.0 |
| Elvanol 52-22 | 11.0–13.5 | 48.3 | 69.0 | 12.0 |
| Gelvatol 20/90 | | 47.2 | 70.0 | 9.0 |
| Vinol 523 | 11–13 | 46.1 | 66.6 | 10.1 |
| Vinol 205 | 11–13 | 41.4 | 61.8 | 7.3 |
| Vinol 325 (crude) | 1.2–2.0 | 46.6 | 77.6 | 4.5 |

From these results the two most appropriate grades of polyvinyl alcohol were selected that fulfilled the following requirements: (a) one yielded a zero receding contact angle on polyethylene despite its relatively high surface tension, (b) the other one had a low surface tension in aqueous solution although it yielded a finite receding contact angle on polyethylene, and (c) the ease of rinsing of the polymer layer adsorbed on polyethylene was also assessed and taken into account.

Elvanol 90—50 and Elvanol 51—05 having been selected, aqueous solutions were prepared from both polyvinyl alcohols, the surface active one [PVAc] and the highly wettable one [PVA]. The concentration was the same for both polyvinyl alcohols for a given experimental series. Mixture of the two polymeric solutions were produced varying the ratios from 1:9 to 9:1 between PVAc and PVA, respectively. The surface tensions and the advancing and receding contact angles of sessile solution droplets on polyethylene were determined for each mixture. Table II contains the results for the constant total polymeric concentration of 1.0 weight percent.

TABLE II

| Volume Ratio of PVA and PVAc Solutions | Surface Tension [mN/m] | Contact Angle (degrees) | |
|---|---|---|---|
| | | Advancing | Receding |
| 10:0 | 62.6 | 78.8 | 0 |
| 9:1 | 46.0 | 71.0 | 15.6 |
| 8:2 | 44.8 | 71.3 | 2.8 |
| 7:3 | 44.4 | 67.8 | 6.8 |
| 6:4 | 45.9 | 64.3 | 7.3 |
| 5:5 | 45.1 | 68.3 | 9.8 |
| 4:6 | 44.3 | 68.3 | 4.6 |
| 3:7 | 43.1 | 61.6 | 12.6 |
| 2:8 | 44.3 | 65.8 | 9.5 |
| 1:9 | 42.4 | 56.5 | 6.4 |
| 0:10 | 41.0 | 68.3 | 15.0 |

On the basis of this measurement series, the most promising ratio of PVA and PVAc was chosen, which had near zero receding contact angle on polyethylene and also had the possible lowest surface tension. As can be seen from the results, the most favorable synergistic ratio must be near to PVAc to PVA ratio of 1:4, because this mixture had the lowest receding contact angle and a reasonably low surface tension.

These measurements were also repeated at lower total polymer concentration for various PVAc and PVA ratios in order to decrease viscosity. At lower polymer concentrations essentially the same synergistic behavior was found as long as the total polymer concentration was greater than 0.1%.

EXAMPLE II

An additional hydrophilic polymer of negligible surface activity and low viscosity with a molecular weight in excess of 30,000 daltons such as Dextran T-40 was added to the synergistic polyvinyl alcohol mixture to increase the oncotic pressure of the preparation to a value of over 40 mmHg. Such a high oncotic pressure was found to have a beneficial effect on damaged epithelium. Furthermore, appropriate buffering agents and preservatives were added while care was taken to maintain total crystalloid osmolality and sodium-potassium ion ratio within the physiological range of the normal aqueous tears. Calcium and magnesium salts were also added at physiological levels.

In the resulting solutions the total content of the polyvinyl alcohols was decreased to the highest possible value where compatibility in the polymeric and electrolyte systems could be achieved yielding a clear and stable solution of reasonably low viscosity. Then the ratio of PVA and PVAc was varied to find out the optimum value where the synergistic effect was the most pronounced in the presence of the other ingredients. Table III contains the data of such a series of experiments.

TABLE III

| Ingredients | Concentration in Perent | | | | | |
|---|---|---|---|---|---|---|
| Dextran T-40 | 4.5 | 4.5 | 4.5 | 4.5 | 4.5 | 4.5 |
| PVA | 0.533 | 0.525 | 0.500 | 0.480 | 0.450 | 0.400 |
| PVAc | 0.067 | 0.075 | 0.100 | 0.120 | 0.150 | 0.200 |

TABLE III-continued

| Ingredients | Concentration in Perent | | | | | |
|---|---|---|---|---|---|---|
| PVAc/PVA | 1:8 | 1:7 | 1:5 | 1:4 | 1:3 | 1:2 |
| NaCl | 0.625 | 0.625 | 0.625 | 0.625 | 0.625 | 0.625 |
| KCl | 0.066 | 0.066 | 0.066 | 0.066 | 0.066 | 0.066 |
| CaCl$_2$* | 0.006 | 0.006 | 0.006 | 0.006 | 0.006 | 0.006 |
| MgCl$_2$* | 0.012 | 0.012 | 0.012 | 0.012 | 0.012 | 0.012 |
| K—sorbate | 0.150 | 0.150 | 0.150 | 0.150 | 0.150 | 0.150 |
| EDTA-Na$_2$ | 0.110 | 0.110 | 0.110 | 0.110 | 0.110 | 0.110 |
| Na$_2$HPO$_4$* | 0.466 | 0.466 | 0.466 | 0.466 | 0.466 | 0.466 |
| Citric acid | 0.025 | 0.025 | 0.025 | 0.025 | 0.025 | 0.025 |
| 1N NaOH [ml] | 0.80 | 0.80 | 0.80 | 0.80 | 0.80 | 0.80 |

*The weight percent figures take into account the crystalline water. Thus dihydrate hexalydrate etc. should be inserted for the respective compound.

Table IV contains the surface tension, receding contact angle values, and the adsorptivity as assessed based on the ease of rinsing obtained with these formulations.

TABLE IV

| PVAc/PVA Ratio | Surface Tension (mN/m) | Receding Angle (degrees) | Adsorptivity (on polyethylene) |
|---|---|---|---|
| 1:8 | 44.3 | 1.8 | negligible |
| 1:7 | 46.3 | 2.9 | very low |
| 1:5 | 43.9 | 1.8 | low |
| 1:4 | 42.7 | 6.4 | considerable |
| 1:3 | 42.3 | 0 | considerable |
| 1:2 | 43.0 | 10.5 | low |

EXAMPLE III

Another additional hydrophilic polymer of low surface activity, low viscosity, and drug-complexing properties; with a molecular weight in excess of 30,000 daltons such as poly(N-vinyl pyrrolidone) (PVP) was added to the synergistic polyvinyl alcohol mixture to increase the oncotic pressure of the preparation to a value over 40 mmHg and to acquire favorable drug-complexing properties. Again, appropriate buffering agents and preservatives were added while care was taken to maintain total crystalloid osmolality and sodium-potassium ion ratio within the physiological range of the normal aqueous tears. Calcium and magnesium salts were also added at physiological levels.

In the resulting solution the total content of the polyvinyl alcohols was kept at a total of 0.4%, which level resulted in sufficient surface activity and a reasonably low viscosity. Then the ratio of PVA and PVAc was varied to find out the optimum value where the synergistic effect was the most pronounced in the presence of the other ingredients. Table V contains some of the pertinent data of such a series of experiments.

TABLE V

| Ingredients | Concentration in Percent | | | | | |
|---|---|---|---|---|---|---|
| PVP | 6.0 | 6.0 | 6.0 | 6.0 | 6.0 | 6.0 |
| PVAc:PVA | 0:10 | 1:9 | 2:8 | 3:7 | 4:6 | 10:0 |
| NaCl | 0.71 | 0.71 | 0.71 | 0.71 | 0.71 | 0.71 |
| KCl | 0.015 | 0.015 | 0.015 | 0.015 | 0.015 | 0.015 |
| CaCl$_2$* | 0.006 | 0.006 | 0.006 | 0.006 | 0.006 | 0.006 |
| MgCl$_2$* | 0.012 | 0.012 | 0.012 | 0.012 | 0.012 | 0.012 |
| K—sorbate | 0.25 | 0.25 | 0.25 | 0.25 | 0.25 | 0.25 |
| EDTA-Na$_2$* | 0.10 | 0.10 | 0.10 | 0.10 | 0.10 | 0.10 |
| NaH$_2$PO$_4$* | 0.0093 | 0.0093 | 0.0093 | 0.0093 | 0.0093 | 0.0093 |
| NaHCO$_3$ | 0.218 | 0.218 | 0.218 | 0.218 | 0.218 | 0.218 |

*The weight percent figures take into account the crystaline water.

Table VI contains the surface tension, advancing and receding contact angle values, and the adsorptivity as assessed based on the ease of rinsing obtained with these formulations.

TABLE VI

| PVAc:PVA Ratio | Surface Tension (mN/m) | Contact Angle (deg.) | | Adsorptivity (polyethylene) |
|---|---|---|---|---|
| | | Advancing | Receding | |
| 0:10 | 62.5 | 82 | 3 | medium |
| 1:9 | 49.1 | 71 | 2 | medium |
| 2:8 | 43.5 | 54 | 4 | considerable |
| 3:7 | 45.0 | 56 | 0 | considerable |
| 4:6 | 47.5 | 54 | 0 | low |
| 10:0 | 47.9 | 72 | 7 | low |

On the basis of these results, a highly physiological artificial tear was formulated that was capable of forming stable thin films over hydrophobic solids and over the corneal epithelium and also serve as an ophthalmic vehicle.

The lipid compatiblity of the final formulations was also studied in the following system:

A small clean trough was filled with saline, another one with a commercial tear substitute, and the third one with our artificial tear. An approximately 100 nanometer thick lipid film was formed over these solutions and its film pressure was determined. The lipid films were visible due to the interference colors. The film pressure was determined and the appearance of the lipid layers was monitored over a time period of 15–20 minutes. The film pressure of the lipid layer was 12 mN/m over saline and 34 mN/m over our artificial tear. In both cases there was no change apparent in these lipid films over the time interval of observation. However, the lipid layer over the commercial tear substitute broke into miniscule lenses and finally disappeared as it became completely solubilized. This experiment confirmed the compatibility of our formulation with, and its beneficial effect on, the superficial lipid layer. The increased film pressure of the lipid layer over the artificial tear will contribute significantly to the stability of the tear film in vivo.

The final formulation was also tested in rabbits and humans. In both species, the formulation readily formed a stable precorneal tear film that exhibited improved stability compared to the natural tear film. The negative stabilizing effect of the added divalent alkali metal salts as was reported by Hecht and Shively (U.S. Pat. No. 4,039,662) was not experienced, most likely due to the unique synergistic mixture of two different polyvinyl alcohols that exhibited vastly improved surface chemical and film-stabilizing properties.

The above examples are not intended to be all inclusive or to limit in any way the application of the invention or the scope of the appended claims.

What is claimed is:

1. An aqueous solution exhibiting a surface tension similar to that of aqueous tears while forming a completely water-wettable absorbed layer over an hydrophobic surface such as glossy polyethylene, which comprises:
   a partially hydrolyzed polyvinyl acetate having at least 73% but no more than 90% of its acetate groups hydrolyzed to alcohol in combination with a fully hydrolyzed polyvinyl alcohol having more than 99% of its acetate groups hydrolyzed to alcohol;
   wherein the weight ratio of partially hydrolyzed polyvinyl acetate to fully hydrolyzed polyvinyl alcohol is within the range from 1:2 to 1:5; and a viscous hydrophilic polymer.

2. The aqueous solution of claim 1, wherein said hydrophilic polymer is poly (N-vinyl pyrrolidone).

3. The aqueous solution of claim 1 which further comprises a drug carried by said hydrophilic polymer.

4. The aqueous solution of claim 1 which further comprises a nutrient carried by said hydrophilic polymer.

* * * * *